(12) United States Patent
Zucker et al.

(10) Patent No.: US 11,143,502 B2
(45) Date of Patent: Oct. 12, 2021

(54) SYSTEMS AND METHODS FOR TEST STRIP INSERTION POSITIONING CHECK AND TYPE MATCH

(71) Applicant: POLYMER TECHNOLOGY SYSTEMS, INC., Whitestown, IN (US)

(72) Inventors: Steven Zucker, Indianapolis, IN (US); Donnie Smith, Indianapolis, IN (US); Christopher Dailey, Whitestown, IN (US); Jonathan Broadwell, Whitestown, IN (US)

(73) Assignee: POLYMER TECHNOLOGY SYSTEMS, INC., Whitestown, IN (US)

( * ) Notice: Subject to any disclaimer, the term of this patent is extended or adjusted under 35 U.S.C. 154(b) by 0 days.

(21) Appl. No.: 16/830,779

(22) Filed: Mar. 26, 2020

(65) Prior Publication Data

US 2020/0309511 A1 Oct. 1, 2020

Related U.S. Application Data

(60) Provisional application No. 62/825,999, filed on Mar. 29, 2019.

(51) Int. Cl.
  *G01B 11/14* (2006.01)
  *B01L 9/00* (2006.01)
  *G01V 8/12* (2006.01)

(52) U.S. Cl.
  CPC ............... *G01B 11/14* (2013.01); *B01L 9/52* (2013.01); *G01V 8/12* (2013.01); *B01L 2300/06* (2013.01)

(58) Field of Classification Search
  CPC ............... G01B 11/14; G01N 35/521; G01N 35/00722; G01N 33/521; G01N 21/8483
  USPC ............................................. 356/615
  See application file for complete search history.

(56) References Cited

U.S. PATENT DOCUMENTS

| | | | |
|---|---|---|---|
| 6,316,264 B1 * | 11/2001 | Corey ................. | G01N 33/521 422/422 |
| 6,525,330 B2 | 2/2003 | Paolini et al. | |
| 6,649,403 B1 | 11/2003 | McDevitt et al. | |
| 8,358,210 B2 | 1/2013 | Goodnow et al. | |
| 9,291,593 B2 | 3/2016 | Elder et al. | |
| 9,488,657 B2 * | 11/2016 | Graham ........... | G01N 35/00722 |
| 2006/0034728 A1 * | 2/2006 | Kloepfer ............ | A61B 5/14532 422/68.1 |
| 2012/0232520 A1 * | 9/2012 | Sloan ..................... | G06F 19/00 604/504 |

(Continued)

OTHER PUBLICATIONS

International Search Report and Written Opinion dated Jul. 21, 2020 issued in corresponding PCT App. No. PCT/US20/24895 (17 pages).

*Primary Examiner* — Hung Nguyen
(74) *Attorney, Agent, or Firm* — Haynes and Boone, LLP

(57) ABSTRACT

In one embodiment, a system for determining the proper positioning of a test strip includes a test strip having a first reading window and a strip holder. The system further includes a meter, the meter receiving and configured to receive the test strip, the meter having a first light source of a first color and a second light source of a second color and a first read window. The meter is configured to illuminate the first light source; detect a first reflectance with the meter through the first read window; and determine if the first reflectance is greater than a no-strip value.

10 Claims, 5 Drawing Sheets

(56) References Cited

U.S. PATENT DOCUMENTS

2014/0170757 A1\* 6/2014 Tsai .................. G01N 21/8483
　　　　　　　　　　　　　　　　　　　436/55
2014/0286550 A1　9/2014 Beule et al.

\* cited by examiner

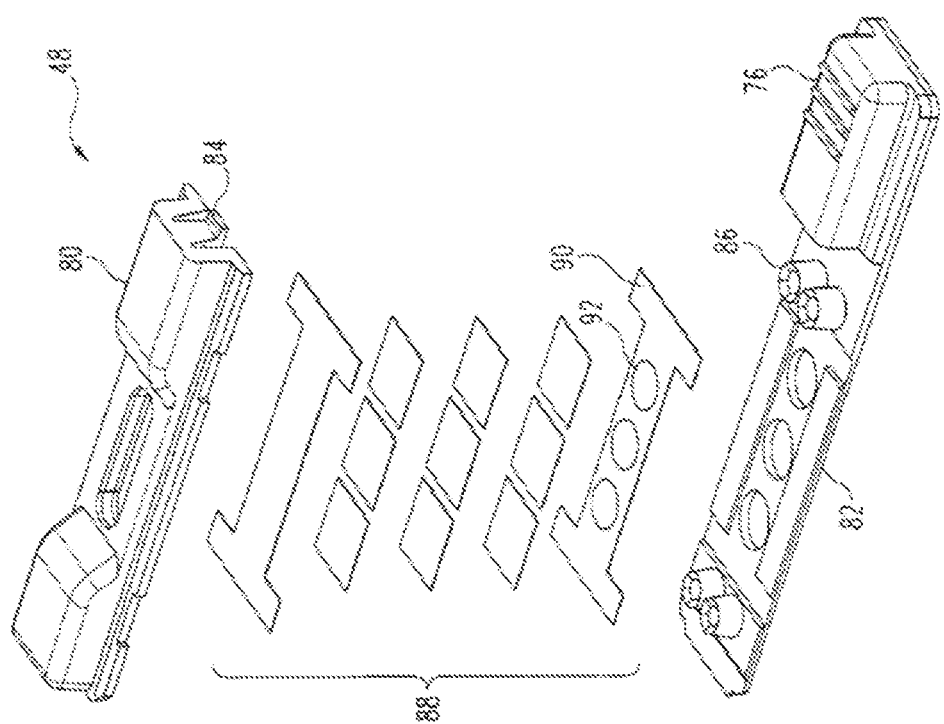

SYSTEMS AND METHODS FOR TEST STRIP INSERTION POSITIONING CHECK AND TYPE MATCH

CROSS REFERENCE

This application claims the benefit of U.S. provisional application No. 62/825,999, filed Mar. 29, 2019, the entirety of which is hereby incorporated by reference.

BACKGROUND

Diagnostic testing devices find usage in many scenarios, including home use, use by a doctor's office, and usage at health fairs. Diagnostic testing devices typically perform testing for various analytes in a bodily fluid and yield results that are equivalent to laboratory testing. Although the devices are designed to be easy to use and reliable, the users of such devices commonly do not follow specific laboratory procedures, have extensive precision and accuracy double checks, and have control procedures. Since the diagnostic testing devices and the methodologies for use are prone to some degree of user error, techniques that decrease the chance of user error are desirable. In the case of diagnostic testing devices employing test strips, a common user error point relates to the proper insertion of the test strip. Therefore, techniques that ensure the proper insertion of the test strip, cassette, or other testing element, in to a meter or reader are desirable.

BRIEF SUMMARY

In one embodiment, a system for determining the proper positioning of a test strip includes a test strip having a first reading window and a strip holder. The system further includes a meter, the meter receiving and configured to receive the test strip, the meter having a first light source of a first color and a second light source of a second color and a first read window. The meter is configured to illuminate the first light source; detect a first reflectance with the meter through the first read window; and determine if the first reflectance is greater than a no-strip value. In one alternative, the no-strip value is 1%. In another alternative, if the first reflectance is less than the no-strip value, then display with the meter a no-strip message. Alternatively, the meter is configured to determine if the first reflectance is in a range of a membrane for testing range, wherein the membrane for testing range is a range of reflectance for an unused properly positioned membrane. In another alternative, the meter is configured to determine if a second reflectance through a second read window of the meter is in a strip holder range. Alternatively, the strip holder range is a range of reflectance from 7% to 10% and is indicative of the reflectance of the strip holder. In another alternative, if the second reflectance is not in the strip holder range, then the meter is configured to display a wrong strip message. Alternatively, if the second reflectance is in the strip holder range, then the meter is configured to display a proceed with test message. In another alternative, if the first reflectance is in a upside down strip range, then the meter is configured to illuminate the second light source and determine whether a third reflectance is greater than an unused test strip reflectance, and if the third reflectance is greater than the unused test strip reflectance, then display with the meter a used strip message and if the third reflectance is not greater than the unused test strip reflectance, then display an upside down strip message. Alternatively, the meter is configured to determine if the first reflectance is in the test holder range and responsive to determining the first reflectance is in the test holder range, displaying a rotate strip message. In another alternative, the meter is further configured to determine that the first reflectance and the second reflectance are not in the test holder range and displaying a foreign object message. Alternatively, the test strip includes a first reading window configured to be aligned with the first read window of the meter. In another alternative, the test strip includes a second read window configured to be aligned with the second read window of the meter.

In one embodiment, a method of determining the proper positioning of a test strip includes providing a test strip having a first reading window and a strip holder. The method further includes providing a meter, the meter receiving and configured to receive the test strip, the meter having a first light source of a first color and a second light source of a second color and a first read window. The method further includes illuminating the first light source. The method further includes detecting a first reflectance with the meter through the first read window. The method further includes determining if the first reflectance is greater than a no-strip value. In one alternative, the no-strip value is 1%. In another alternative, if the first reflectance is less than the no-strip value, then displaying with the meter a no-strip message. Alternatively, the method further includes determining if the first reflectance is in a range of a membrane for testing range, wherein the membrane for testing range is a range of reflectance for an unused properly positioned membrane. Alternatively, the method further includes determining if a second reflectance through a second read window of the meter is in a strip holder range. Alternatively, the strip holder range is a range of reflectance from 7% to 10% and is indicative of the reflectance of the strip holder. In another alternative, if the second reflectance is not in the strip holder range, then displaying a wrong strip message. Alternatively, the method further includes if the second reflectance is in the strip holder range, then displaying a proceed with test message. Alternatively, the method further includes if the first reflectance is in a upside down strip range, then illuminating the second light source and determine whether a third reflectance is greater than an unused test strip reflectance, and if the third reflectance is greater than the unused test strip reflectance, then displaying with the meter a used strip message and if the third reflectance is not greater than the unused test strip reflectance, then displaying an upside down strip message. Alternatively, the method further includes determining if the first reflectance is in the test holder range and responsive to determining the first reflectance is in the test holder range, displaying a rotate strip message. Alternatively, the method further includes comprising determining that the first reflectance and the second reflectance are not in the test holder range and displaying a foreign object message. In one alternative, the test strip includes a first reading window configured to be aligned with the first read window of the meter. In another alternative, the test strip includes a second read window configured to be aligned with the second read window of the meter.

BRIEF DESCRIPTION OF THE DRAWINGS

FIG. 2 shows one embodiment of a test strip;

DETAILED DESCRIPTION

Certain terminology is used herein for convenience only and is not to be taken as a limitation on the embodiments of the systems and methods for test strip insertion positioning check and type match. In many embodiments, systems and methods for test strip insertion positioning check and type match utilize a color detection system to determine whether a test strip is inserted into a meter correctly and whether the test strip is the correct type of strip. In many scenarios the test strips associated with a meter are color coded such that a test strip that tests for a certain analyte has a certain color. In many scenarios, the test strips include a reading window in a test strip holder body. The reading window provides access to view a portion of the reaction membrane or other membrane where a color change occurs during testing. The meter typically shines a light through the reading window of the test strip in order to read/detect the color change that occurs during the testing. For background, the color change is typically produced by an analyte of interest reacting with chemicals in the membranes of the test strip. The analyte of interest may be any of a large variety of analytes, including but not limited to: lipids (HDL, LDL, Triglycerides, Total Cholesterol), glucose, creatinine, Hemoglobin, Hemoglobin A1C, various proteins, antibodies, and other indicators. In many embodiments, the test strip receives a bodily fluid, such as blood, urine, or saliva, or other fluid or tissue sample.

Figure 1:
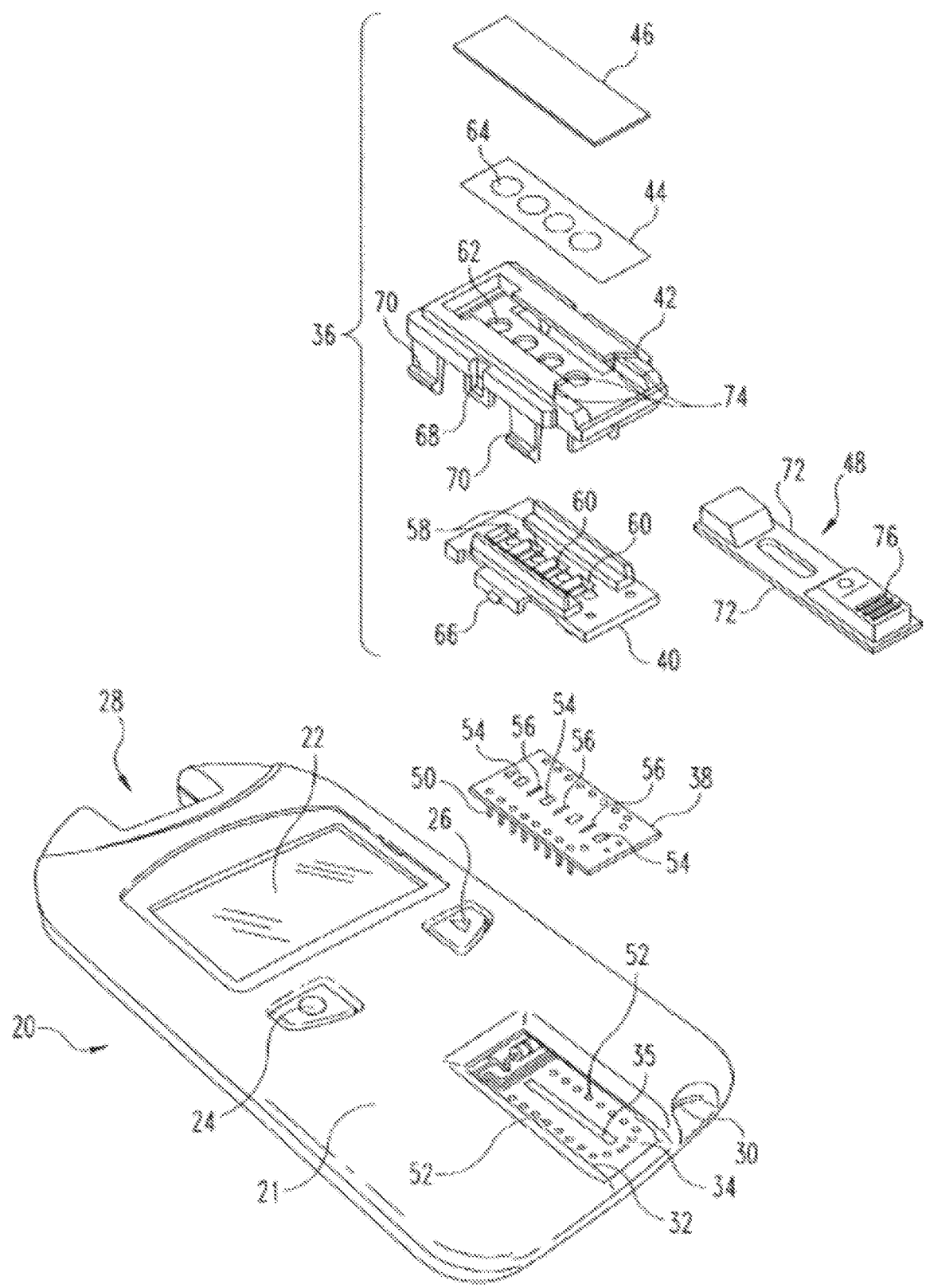
FIG. 1 shows one embodiment of a meter and test strip combination.

FIG. 1 shows one embodiment of a device that may be used with the systems and methods for test strip insertion positioning check and type match. Meter 20 includes a body 21, a display 22, button 24 and 26, a port 28, which receives a chip storing calibration information and other testing related information (sometimes known as a Memo chip) (not shown), a port 30 for an amperometric test strip (not shown), and an opening 32. In the inside of meter 20 is the main circuit board 34 and compression spacer 35, part of which can be seen in opening 32. Optical block 36 includes optical hybrid chip 38, light shield 40, strip holder 42, die cut adhesive 44, and glass 46. Finally, a test strip 48 is inserted into holder 42.

Chip 38 has pins 50 that are received into holes 52 in circuit board 34 by soldering or other fastening means known in the art. Chip 38 includes photodiodes 54 and LED arrays 56. Photodiodes 54 align with openings or pores 58 in light shield 40 while LED arrays 56 align with rectangular openings 60 in light shield 40. In turn, pores 58 align with the direct center of respective holes 62 and 64 in strip holder 42 and adhesive 44, respectively. Rectangular openings 60 align with the sides of holes 62 and 64 so that the incident beam is directed to the relevant portions of test strip 48 at an angle so that reflectance can be measured.

Conveniently, optical hybrid chip 38 is first positioned and inserted into main circuit board 34 on top of compression spacer 3. In turn, light shield 40 snaps into strip holder 42 by means of tabs 66 that are received in corresponding openings 68 as shown. Glass 46 is secured to strip holder 42 by adhesive 44 or other suitable means known in the art. The entire optical block assembly 36, once fastened together, snaps into the main circuit board 34 by means of legs 70 that bias outwardly and engage the side of an oblong opening in the main circuit board 34. Compression spacer 35 serves the purpose of compressing the optical hybrid chip 38 into light shield 40 to maintain minimal deviation of mechanical stack-up in the optical block assembly. After the optical block subassembly is firmly affixed into main circuit board 34, optical hybrid chip 38 is soldered into place on the opposite side (not shown).

When installed in meter 20, holder 42 of optical block 36 receives test strip 48. More specifically, sides 72 of test strip 48 are fittingly received into grooves 74 of holder 42. A handle portion 76 aids the user in inserting the strips 48 into the instrument.

Turning now to FIG. 2, test strip 48 may be formed by injection molding. Test strip 48 includes handle 76 and top portion 80, which in some scenarios is hingedly attached to bottom portion 82. Top portion 80 includes a leg member 84 that is inserted into a corresponding opening (not shown) in portion 82 and thereby secures top portion 80 to bottom portion 82. The other side of top portion 80, as mentioned, may be hingedly attached to bottom portion 82. Bosses 86 receive complementary pegs (not shown) that extend downwardly from top portion 80 and produce a snap-fit engagement of top portion 80 to bottom portion 82. Other attachment mechanisms are possible, such as snap fit, glue, welding, etc. Test matrix 88 has an adhesive layer 90 having openings 92 is used to hold the matrix together during assembly. Note that bottom portion 82 includes multiple apertures which may be referred to as reading windows. These reading windows line up with holes 62, 64 in strip holder 42 and adhesive 44 when the test strip 48 is slid into place.

When light shines through holes 62, 64 from LED arrays 56, it will generally illuminate whatever is in its path. The light will be reflected back to photodiodes 54 where it may be detected. If the strip 48 is properly aligned, then prior to dosing the strip 48, the test matrix 88 will have its default or unreacted color. This color is generally colorless or some shade of white/off-white. If the strip is mis-aligned, the light will strike the bottom portion 82 (or partially strike the bottom portion), which is opaque and may be color coded according to the test that the strip 48 performs. If there is no strip in the device, then generally the ambient light will be detected by the photodiodes 54. By distinguishing between the light received in the photodiodes 54, the systems and methods for test strip insertion positioning check and type match may be practiced. The scenario provided is merely an example of a system oriented to perform the systems and methods for test strip insertion positioning check and type match.

In many embodiments, characteristics of systems employing the systems and methods for test strip insertion positioning check and type match include some similar characteristics. Generally, the systems include a test device that is received by a meter. The meter includes a light detecting device and in many scenarios a light producing device. The test device includes a reading area where a color change occurs in response to an analyte. The test device includes a holder portion. The color of the holding portion and the color of the reading area are not the same. The holding portion may be of a variety of different colors.

Figure 3A:
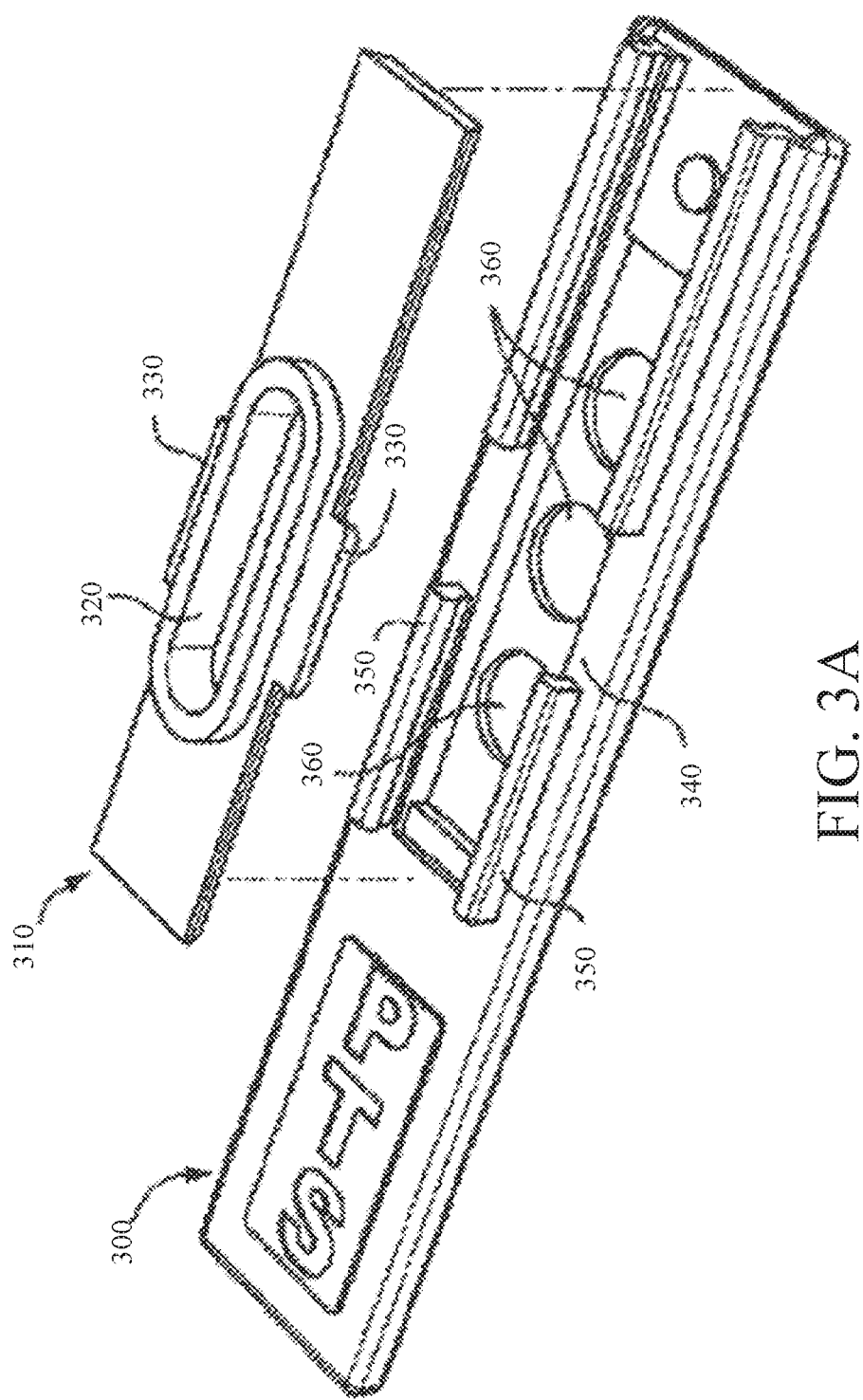
FIG. 3A shows another embodiment of a test strip.

FIG. 3A shows another embodiment of a test strip holder 300 for use with a meter, such as meter 20. Similar to in the previously described test strip, test strip holder 300 may hold a test membrane, which is visible through aperture or reading windows 360 as well as sample port 320. Reading windows 360 are designed and positioned to line up over the holes 62, 64 of the test strip. Additionally, the test strip holder 300 is designed to include a cap 310 that pressure fits via pressure fit wings 330 and apertures 340 in sides 350. In contrast to the previous strip 48, strip 300 has a low profile, so it is prone to being inserted upside down. Due to the thickness of the strip, it is positioned slightly away from the holes 62, 64 that provide for illumination and reading of the strip, since sides 350 raise the strip 300 slightly. This is in contrast to a scenario where it is inserted backwards and the bottom of the strip will sit closer to the holes 62, 64. Also, in an upside down as compared to backwards configuration, some of the sample port may be positioned in the line of sight of the holes 62, 64.

Figure 3B:
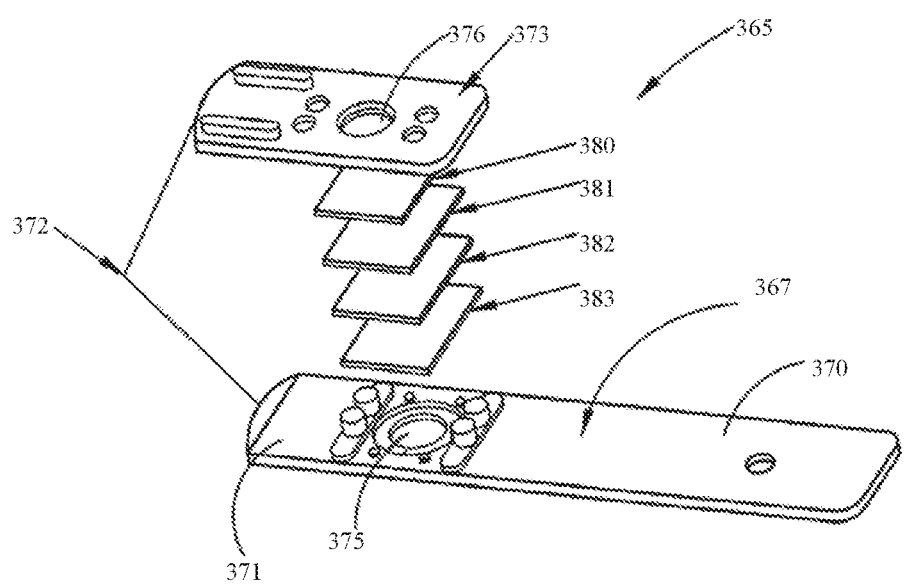
FIG. 3B shows another embodiment of a test strip.

In FIG. 3B, a single analyte test strip 365 includes test strip holder 367. Test strip 365 may be plastic and formed via injection molding. The test strip holder 367 may have a certain color that may vary according to the type of test strip used for detection under the methods described herein. Test strip holder includes handle 370 and end portion 371 which is preferably hingedly attached by hinge portion 372 to second end portion 373, shown exploded away in FIG. 1. Portion 371 is foldable about hinge portion 372 over portion 373 as shown. End portion 371 includes an opening 375 while end portion 373 includes a complementary spaced opening 376. When end portion 373 is folded over end portion 371, openings 375 and 376 are aligned. In its folded position, opening 376 in holder 373 defines an application window for depositing a body fluid sample while opening 375 defines a test reading window in which optoelectronic measurements of chemistry test reactions are conducted. Generally, in use, the opening 375 will be aligned over the first hole/reading window of the meter 20 described in FIG. 1. Many of the methods below are for determining when the opening 375 is not aligned over the first window.

In one example, strips for the CardioChek PA and Plus meters can be improperly inserted into the CardioChek PA and Plus meters such that the analyte sensitive chemistry would not be visible to the optical block. Software mitigation strategies offer an efficient solution to this risk. For example, in some meter and strip combinations, the strip can be inserted backwards or upside down and the meter will still prompt the user to apply the sample. The resulting reading would not be of the chemistry and therefore would report an incorrect value. These mitigation strategies will further reduce the risk of an incorrect reading being reported.

This mitigation strategy can identify the orientation of the test strip. Once each assay is fully characterized, the software flashes the appropriate LED(s) to determine if the strip is correctly positioned on the meter. It would then possible to instruct the user if the strip was upside-down, backwards, or both. Since this check would occur prior to the instructions of dosing the strip, the risk of an incorrect result would be mitigated. In addition, the error notification could instruct the user on how to correct the orientation and therefore reduce the number of wasted strips and eliminate potential frustration of the user.

It is also possible to verify that the correct strip was being used for each assay. Once the strip orientation is confirmed, the second window can be utilized to ensure that the color of the carrier is matched appropriately. In this scenario, each assay holder has a unique color associated with it. In order to differentiate all of the colors currently being used by PTS Diagnostics, it may be required to use both the red and green LEDs to verify the color of the strip carrier.

The new logic sequence for the meters can be leveraged to every reflectance assay involving meters and test strips, such as the ones by PTS Diagnostics. In many embodiments, the techniques are applied to other embodiments, utilizing a wide variety of test strip holders and meters. Exemplary systems are described above in relation to FIGS. 1-3.

Modifications include to the cutoff thresholds based on the color of the membrane and carrier and can be set as a parameter using the memo chip. The current logic drives the LEDs to flash and prints "Insert Strip" on the screen as long as the reflectance is below a threshold. At this point the meter will instruct the user to "Apply Sample". There is a risk that the user can be instructed to apply the sample to the strip even though the strip is not properly positioned on the CardioChek device. If the strip is upside-down, backwards, previously used, or even a different strip made for a different assay, many current versions of software will still instruct the user to dose the strip. Once this happens any result that is printed on the screen will be incorrect and could lead to making incorrect medical decisions or taking unnecessary medication.

In principle, the initial logic sequence of running meters remains similar, however, the instructions to apply sample will not appear on the meter until a series of additional checks are performed. Typically, meters have a set of instructions that are displayed informing the user when to apply a sample, what steps to take, and when to read the result, etc.

In many embodiments, the first step is to detect whether the detected light is the same as with no strip inserted. At this point, any reflectance less than 1% is indicative of nothing on top of the optical block and the meter will display "Insert Strip". The meter will continue to flash the LED in at least one of the windows and measure the reflectance every second until the reflectance in the first two windows is greater than 1%. In many embodiments, in order to proceed to the "Apply Sample" step, the reflectance will have to be within a narrow margin defined in the programming. In addition, at this stage the sequence can include a check to make sure that the inserted strip has the correct chemistry for the analysis. Each of the assays manufactured at PTS Diagnostics has a unique color. In many embodiments, the test devices (test strips) have a unique color. Each colored strip is characterized and the reflectance (using either the green or red LED depending on the situation) must be within the narrow band to confirm that the correct strip is being used. When the first two windows measure a value within the appropriate ranges will the testing proceed, and the user will be instructed to apply the sample. This will prevent the possibility of the user receiving an incorrect test result as a consequence of inserting the strip incorrectly or inadvertently using the wrong test strip.

Figure 4:
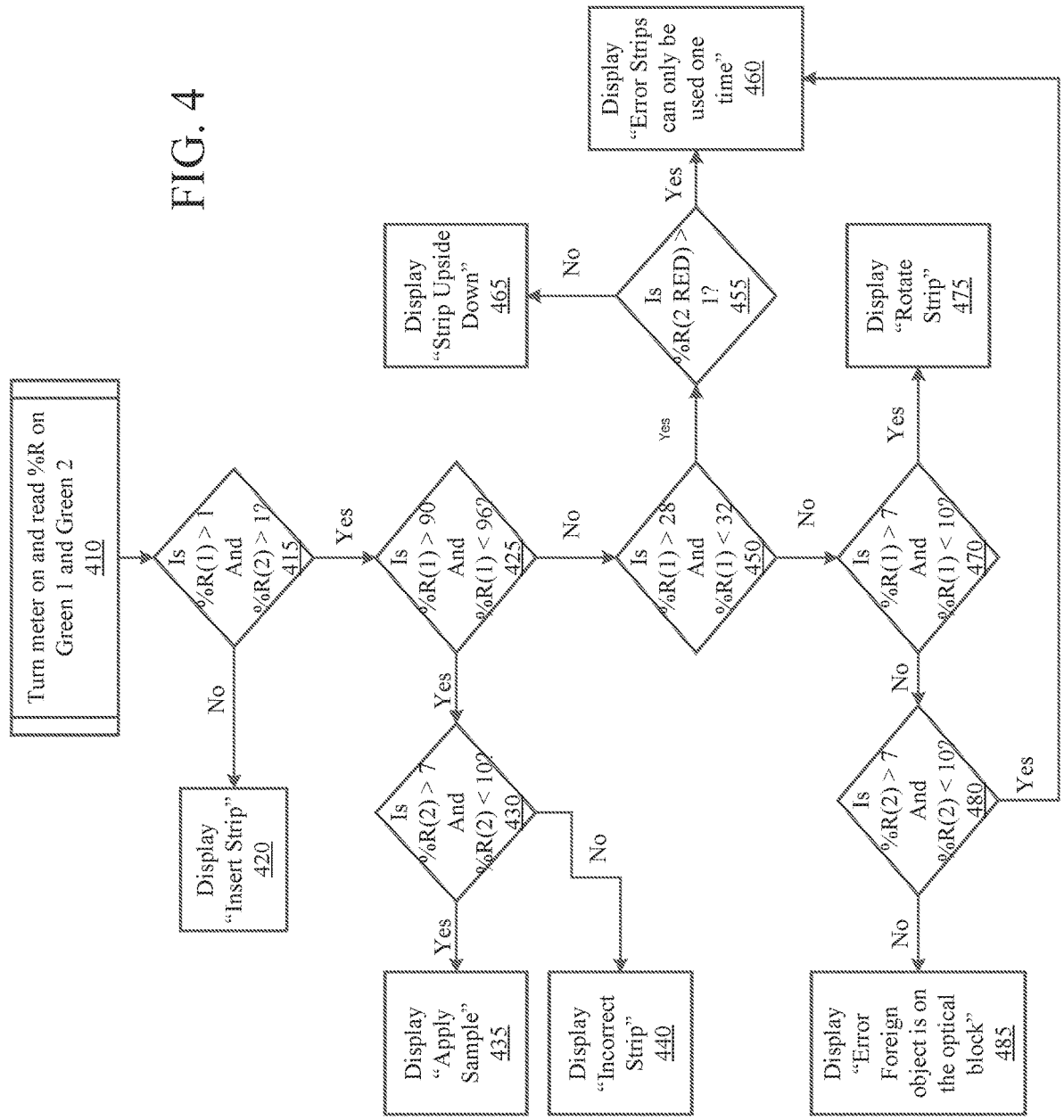
FIG. 4 shows one embodiment of a method for test strip insertion positioning check and type match.

FIG. 4 contains an example logic sequence that could be used to identify each of the six potential situations when operating a meter and test strip combination, such as either the CardioChek PA or Plus meters. The first two scenarios, both discussed above, are when the correct strip has been properly inserted into the analyzer or if an incorrect strip was properly inserted into the analyzer. If the reflectance in a first window does not match the reflectance of the clean white membrane, the next two checks are to see if the reflectance matches with having the strip backwards, backwards and upside-down, or upside-down. If the strip is forced into the analyzer upside-down, then the reflectance of the first window will be lower than the properly positioned strip. The narrow range of upside-down strips overlaps with the wide range of previously dosed strips. Each test strip is designed to be used a single time and must be measured immediately after dosing. The measured reflectance changes over time as the membrane dries and within 24 hours appears to return to the original color. However, with the coat of red blood cells on the separation layers, there is a measurable difference between new strips and previously dosed strips. This reflectance temporarily overlaps the reflectance of upside-down strips, but the two situations can be identified with use of a second window. Since the upside-down strip will not be flush with the optical block, there is a significant difference between the reflectance compared with the previously dosed strip that is properly inserted.

The two backwards orientations would both position the colored carrier directly above the optical block and therefore it can be analyzed the same way the strip was identified in the second window. If the carrier is above the first window, an error code can be used to instruct the user to rotate the strip to the proper orientation. Finally, if none of these parameters are met, the reflectance at the second window is measured again. If the strip is the correct color, then it is concluded that the strip was previously dosed. However, if the object does not align with the color of the carrier on the second window, then the object on the optical block is likely something other than the intended test strip (PTS Diagnostics test strip).

Therefore, in many embodiments, in a first step the meter checks to see if a strip has been properly inserted. The system does this by shining a light and measuring the reflectance generated. If the reflectance is the expected value, then the testing proceeds. Typically, this is done by measuring the reflectance of known strips (those having a clean white membrane) and then calibrating the meter to detect as for this value.

In the second step, the meter checks to see if the proper assay has been inserted to match the RAM chip (Memo chip) that is being used. This is done on the basis of the color of the test strip. Since each test strip will have a particular assay color, the meter will measure the reflectivity of the strip, through in some scenarios, the fourth port that does not line up with any of the test window or based on the color change provided by the ports that line up with the test windows.

In the third set of steps, the meter determines whether the strip is backwards, backwards and upside-down, upside-down, or previously dosed. This may be calibrated based on previous testing and calibration done in the lab prior to distribution of the meter, to determine what the range of readings are for each scenario.

FIG. 4 shows one embodiment of a method of determining whether the strip is properly inserted. It is important to realize in many scenarios, the meter includes red and green emitting LEDs. Furthermore, there are multiple read windows. As shown in FIG. 1, read window 1 is located closest to the meter screen 22. Read window 2 is located one hole further from the meter screen 22. In step 410, Green LED 1 and Green LED 2 are activated for windows 1 and 2. If the reflectance, is the detectors of both meters is greater than 1 in step 415 then that means there is an object in the slot of the meter. If the reflectance is not greater than 1, then there is likely nothing in the slot. In such a scenario, the method proceeds to step 420 where the meter indicates to the user via the screen that the strip is to be inserted.

The method then proceeds to step 425. In step 425, the meter determines whether the reflectance is greater than 90% but less than 96% in read window 1. This is indicative of the white reflective membrane being properly position in read window 1. If this is the case, then the method proceeds to step 430 where it is determined what the reflectance is in read window 2. In the scenario of FIG. 4, read window 2 corresponds to the second read window position. In the example of the method, the strip inserted does not have a membrane at the second read window position. Therefore, the meter should read a low level of reflectivity for testing to begin. If this is the case, then the meter indicates in step 435 to apply the sample. Then the meter performs the testing method. If the reflectivity is higher, then in step 440, the meter indicates that the wrong test strip has been inserted. Note, that the test strips shown in the present application have three reading windows. In the test strip that is subject to the method of FIG. 4, the test strip merely has a single reading window, the window closes to the screen of the device. Numerous alternatives are possible for test strips. Test strips may have one, two, three, or more reading windows. Of course, different meters may have different number of read windows that may correspond to test strips having different numbers of reading windows. Generally, for each reading window that is intended to be in the test strip, that reading window should have a high reflectance. This reflectance may exemplarily be greater than 90% but less than 96%, but may be any reflectance corresponding to the unused membrane of the test strip.

In step 450, the reflectance of the read window is again measured and if the reflectance is more than 28 but less than 32, then it is determined that the strip has either been already used or is upside down. In step 455, instead of the green light being activated, the red light is activated. If the reflectance under the red light is greater than 1, then this indicates that the test strip has already been used and the flow proceeds to step 460. In step 460, the meter displays that the strip has already been used. Otherwise, it is determined based on the reflectance, that the strip is upside down in step 465 and the user is notified by the meter as such.

If in 450 the answer is no, then the flow proceeds to step 470, where it is determined whether the reflectance in read window 1 is between 7 and 10 and whether, in step 480, the reflectance in read window 2 is between 7 and 10. If the answer is no, then that indicates that both windows are blocked by a foreign object and the method proceeds to step 485 where the user is notified through the meter as such. Otherwise, in in step 470 it is determined that the reflectance in read window 1 is between 7 and 10, then the strip should be rotated. If it is determined in step 470 that the reflectance of the read window 1 is between 7 and 10 and that in step 480 the reflectance of read window 2 is not between 7 and 10, then this indicates the strip has been used before and the method proceeds to step 460.

The point of this method, is that if the reflectance is very low (for example less than 1) then there is likely no test strip. This is especially true if more than one window indicates that there is not reflectance. The it is determined whether the proper number of windows return that there is high reflectance (for example upwards of 90%) in reading windows where there are supposed to be membranes that will change color. If there are the right number, then the user is informed that the sample should be applied. If not, then the user is notified that the strip is wrong. If the reflectance is not high in the expected read windows, then that indicates some sort of error condition. Therefore, the system attempts to determined what the error condition is. Generally, a higher reflectance in the green wave length, will indicate that either the strip is upside down or already used. This is generally in the range of 28% to 32%. If when analyzed with red light, the reflectance is low, then it is likely that the strip is upside down and if the reflectance is greater than 1, the strip has likely already used (due to residual hematocrit from previous testing). If the reflectance is lower, then this generally indicates that the test strip is inserted incorrectly or a foreign object is in the meter. If neither read window 1 or 2 has a reflectance representative of the strip being inserted backwards or perhaps that the strip is already used. Otherwise, a foreign object is likely.

In one alternative, a multianalyte strip is used that may be inserted upside down. This may not apply to many test strips, including current PTS Diagnostics multianalyte strips, since they may not be insertable upside down. Therefore, in for a multi-analyte version that is insertable upside down, the system would first attempt to detect whether port 1 has the high degree of reflectance (+90%) that suggests a membrane is located in the first slot. Then the system would attempt to detect whether port 2 has the high degree of reflectance (+90%) that suggests a membrane is located in the second slot. If not, then it is likely the strip is not properly inserted and probably needs to be rotated or it is a single analyte strip. Then the system would attempt to detect whether port 3 has the high degree of reflectance (+90%) that suggests a membrane is located in the third slot. If not, then the strip likely needs to be rotated or it is a single analyte strip. In relation to foreign object detection, if two of the panels do not show a reflectivity corresponding to an upside down test strip or the reflectivity of the test strip holder, then it is likely a foreign object. In such a way, the basic method may be adapted for a multi-analyte test strip.

In another embodiment, slightly larger test strips are used that are not insertable upside down. For these strips, the size is slightly larger than the single-analyte strip, and the users are not able to force it in upside-down. No measurements are required to prevent this use case, because it is impossible to push the strip in this direction, and therefore the portion of the logic sequence that concludes an upside-down strip should be removed for the multi-analyte strips. In many configurations, the first three windows should all be within that 90-96 reflectance range, and the fourth should be within the range of the color of the plastic. In this case the multi-analyte strips are all black, but similar to the comments made about the dark blue strips (between 7 and 10% reflectance), that should be used as an example that can be leveraged into other colors. Please note that in the various embodiments described herein, the reflectance provided for (between 7 and 10% reflectance) is dependent on the color of the test strip holder and may vary. In many configurations, the logic would provide for window 4 to be within 7 and 10% reflectance upon a proper insertion. If not, then the strip likely needs to be rotated or it is a single analyte strip. Foreign object detection and missing strip would function similarly, however, since the strip may not be able to be physically inserted upside down, this test may not be needed.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

In various instances, parts of the method may be implemented in modules, subroutines, or other computing structures. In many embodiments, the method and software embodying the method may be recorded on a fixed tangible medium.

While specific embodiments have been described in detail in the foregoing detailed description, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for determining the proper positioning of a test strip, the system comprising:
   a test strip having a first reading window and a strip holder;
   a meter, the meter receiving and configured to receive the test strip, the meter having a first light source of a first color and a second light source of a second color and a first read window, wherein the meter is configured to illuminate the first light source;
   detect a first reflectance with the meter through the first read window;
   determine if the first reflectance is greater than a no-strip value;
   wherein the no-strip value is 1%;
   wherein if the first reflectance is less than the no-strip value, then display with the meter a no-strip message;
   wherein the meter is configured to determine if the first reflectance is in a range of a membrane for testing range, wherein the membrane for testing range is a range of reflectance for an unused properly positioned membrane;
   wherein the meter is configured to determine if a second reflectance through a second read window of the meter is in a strip holder range;
   wherein the strip holder range is a range of reflectance from 7% to 10% and is indicative of the reflectance of the strip holder;
   wherein if the second reflectance is not in the strip holder range, then the meter is configured to display a wrong strip message;
   wherein if the second reflectance is in the strip holder range, then the meter is configured to display a proceed with test message;
   wherein if the first reflectance is in a upside down strip range, then the meter is configured to illuminate the second light source and determine whether a third reflectance is greater than an unused test strip reflectance, and if the third reflectance is greater than the unused test strip reflectance, then display with the meter a used strip message and if the third reflectance is not greater than the unused test strip reflectance, then display an upside down strip message.

2. The system of claim 1, wherein the meter is configured to determine if the first reflectance is in the test holder range and responsive to determining the first reflectance is in the test holder range, displaying a rotate strip message.

3. The system of claim 2, wherein the meter is further configured to determine that the first reflectance and the second reflectance are not in the test holder range and displaying a foreign object message.

4. The system of claim 3, wherein the test strip includes a first reading window configured to be aligned with the first read window of the meter.

5. The system of claim 4, wherein the test strip includes a second read window configured to be aligned with the second read window of the meter.

6. A method of determining the proper positioning of a test strip, the method comprising:
prov101ding a test strip having a first reading window and a strip holder;
providing a meter, the meter receiving and configured to receive the test strip, the meter having a first light source of a first color and a second light source of a second color and a first read window;
illuminating the first light source;
detecting a first reflectance with the meter through the first read window;
determining if the first reflectance is greater than a no-strip value;
determining if the first reflectance is in a range of a membrane for testing range, wherein the membrane for testing range is a range of reflectance for an unused properly positioned membrane;
determining if a second reflectance through a second read window of the meter is in a strip holder range;
wherein the no-strip value is 1%;
wherein if the first reflectance is less than the no-strip value, then displaying with the meter a no-strip message;
wherein the strip holder range is a range of reflectance from 7% to 10% and is indicative of the reflectance of the strip holder;
wherein if the second reflectance is not in the strip holder range, then displaying a wrong strip message;
wherein if the second reflectance is in the strip holder range, then displaying a proceed with test message;
wherein if the first reflectance is in a upside down strip range, then illuminating the second light source and determine whether a third reflectance is greater than an unused test strip reflectance, and if the third reflectance is greater than the unused test strip reflectance, then displaying with the meter a used strip message and if the third reflectance is not greater than the unused test strip reflectance, then displaying an upside down strip message.

7. The system of claim 6, further comprising determining if the first reflectance is in the test holder range and responsive to determining the first reflectance is in the test holder range, displaying a rotate strip message.

8. The system of claim 7, further comprising determining that the first reflectance and the second reflectance are not in the test holder range and displaying a foreign object message.

9. The system of claim 8, wherein the test strip includes a first reading window configured to be aligned with the first read window of the meter.

10. The system of claim 9, wherein the test strip includes a second read window configured to be aligned with the second read window of the meter.

* * * * *